United States Patent [19]

Buzby, Jr. et al.

[11] Patent Number: 4,698,445
[45] Date of Patent: Oct. 6, 1987

[54] 4-AMINO BENZENESULFONAMIDES

[75] Inventors: George C. Buzby, Jr., Blue Bell; Thomas J. Colatsky, Paoli, both of Pa.

[73] Assignee: American Home Products Corporation, New York, N.Y.

[21] Appl. No.: 875,816

[22] Filed: Jun. 18, 1986

[51] Int. Cl.$^4$ .......................................... C07C 143/80
[52] U.S. Cl. ...................................................... 564/86
[58] Field of Search ........................................ 564/86

[56] References Cited

U.S. PATENT DOCUMENTS 2,233,296 2/1941 Nelles et al. ............................ 564/96
3,580,949 5/1971 Gruenman et al. ................... 564/96

FOREIGN PATENT DOCUMENTS 1912848 10/1969 Fed. Rep. of Germany .
47-37413 9/1972 Japan .
1053204 12/1966 United Kingdom .

OTHER PUBLICATIONS

Silberg et al, "Chem. Abstracts," vol. 55, (1961) 8402i.
Riccieri et al, "Chem. Abstracts," vol. 56, (1962) 5954e.
Silberg et al., ACAD Rep Populace Romire, Fillala Clug, Studee Cercetari Med., 10, 241–252 (1959).
Bexton et al., Pharmac. Ther. 17, 315-55 (1982).
Vaughan-Williams, J. Clin. Pharmacol. 24, 129-47 (1984).
Thomis et al., Ann. Rep. Med. Chem. 18, 99–108 (1983).
Fleckenstein, Ann. Rev. Pharmacol., 17, 149–66 (1977).

*Primary Examiner*—Anton H. Sutto
*Attorney, Agent, or Firm*—Richard K. Jackson

[57] ABSTRACT

N-Aminoalkyl(aminophenyl)sulfonic acid amides of the formula:

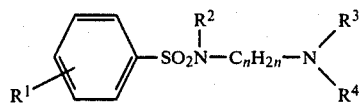

in which
$R^1$ is —$NH_2$, alkylamino of 1 to 3 carbon atoms or alkanoylamino of 2 to 4 carbon atoms, in 3- or 4-position of the benzene ring;
$R^2$ is hydrogen or alkyl of 1 to 4 carbon atoms;
$R^3$ is hydrogen or straight or branched chain alkyl of 1 to 4 carbon atoms;
$R^4$ is straight or branched chain alkyl of 1 to 4 carbon atoms; with the proviso that $R^3$ and $R^4$ are branched chain alkyl when $R^2$ is hydrogen;
and n is one of the integers 2, 3 or 4;
or a pharmaceutically acceptable salt thereof, an antiarrhythmic agents useful in the treatment of cardiac arrhythmias and conditions characterized by coronary arteries vasospasm.

12 Claims, No Drawings

4-AMINO BENZENESULFONAMIDES

BACKGROUND OF THE INVENTION

Class III anti-arrhythmic agents may be categorized as having the ability to markedly prolong dog Purkinje fiber action potential duration without producing significant changes in maximal upstroke velocity. Unlike Class I anti-arrhythmic agents, a pure Class III agent displays no effects on cardiac sodium channels. The electrophysiologic properties of a compound defining a Class III activity profile are observed in vivo as negligible effects on atrial, ventricular and H-V conduction line while producing a marked increase (greater than 20 percent) in both the atrial and ventricular refractory period. In contrast, Class I agents will demonstrate a marked slowing of ventricular conduction velocity without significant changes in the refractory period. Recent reviews of these agents are by Bexton et al., Pharmac. Ther. 17, 315–55 (1982); Vaughan-Williams, J. Clin. Pharmacol. 24,129–47 (1984) and Thomis et al., Ann. Rep. Med. Chem. 18, 99–108 (1983).

DESCRIPTION OF THE INVENTION

In accordance with this invention there is provided a group of antiarrhythmic agents of the formula:

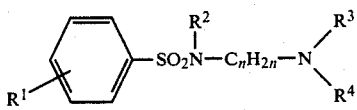

in which
$R^1$ is $-NH_2$, alkylamino of 1 to 3 carbon atoms or alkanoylamino of 2 to 4 carbon atoms, in 3- or 4-position of the benzene ring;
$R^2$ is hydrogen or alkyl of 1 to 4 carbon atoms;
$R^3$ is hydrogen or straight or branched chain alkyl of 1 to 4 carbon atoms;
$R^4$ is straight or branched chain alkyl of 1 to 4 carbon atoms; with the proviso that $R^3$ and $R^4$ are branched chain alkyl when $R^2$ is hydrogen;
and n is one of the integers 2, 3 or 4;
or a pharmaceutically acceptable salt thereof.

Based upon the presence or absence of an alkyl substituent on the sulfonamide nitrogen and branched chain alkylation of the terminal nitrogen atom, the compounds of the above-described genus are further characterized as a preferred group of compounds as follows:

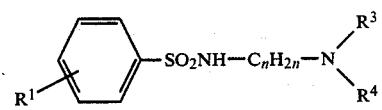

in which
$R^1$ is $-NH_2$ or, when $R^3$ and $R^4$ are both alkyl, alkanoylamino of 2 to 4 carbon atoms in 3- or 4-position of the benzene ring;
$R^3$ is hydrogen or branched chain alkyl of 3 or 4 carbon atoms;
$R^4$ is branched chain alkyl of 3 or 4 carbon atoms;
and n is one of the integers 2, 3 or 4;
or a pharmaceutically acceptable salt thereof.

The most preferred compounds are those containing a sulfonamide nitrogen alkyl substituent as follows:

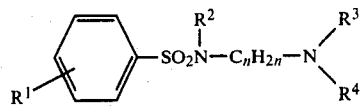

in which
$R^1$ is $-NH_2$, alkylamino of 1 to 3 carbon atoms, alkanoylamino of 2 to 4 carbon atoms in 3- or 4-position of the benzene ring;
$R^2$ is alkyl of 1 to 4 carbon atoms;
$R^3$ is hydrogen or branched chain alkyl of 3 or 4 carbon atoms;
$R^4$ is branched chain alkyl of 3 or 4 carbon atoms;
and n is one of the integers 2, 3 or 4;
or a pharmaceutically acceptable salt thereof. Within this subgenus, the most highly or a pharmaceutically acceptable salt thereof. Within this subgenus, the most highly preferred variables reside in the isopropyl alkyl substituent when present and representing $R^2$, $R^3$ and $R^4$, $R^1$ as $-NH_2$ in 4-position of the benzene ring and n equal to 2.

The pharmaceutically acceptable salts of the antiarrhythmic agents of this invention are prepared directly by neutralization of the free base. These physiologically acceptable salts may be formed with organic or inorganic acids such as hydrochloric, hydrobromic, phosphoric, sulfuric, sulfamic, nitric, methylsulfonic, acetic, maleic, succinic, fumaric, tartaric, citric, salicylic, lactic, naphthalenesulfonic acid, and the like.

The compounds of this invention are prepared by reaction of a nitro substituted benzene sulfonyl halide with an appropriately substituted α, ω-alkane diamine of 2 to 4 carbon atoms. These reactants are generally known compounds and otherwise are routinely prepared by techniques well within the skill of the chemist.

The compounds of this invention demonstrate antiarrhythmic activity when tested in the standard experimental animal in accordance with the following procedure:

Rats weighing between 400–500 gms were anesthetized with 35–40 mg/kg sodium pentobarbital intraperitoneally. Rats were close-clipped on the neck and left thorax prior to cannulation of the jugular vein and carotid artery for measurement of arterial blood pressure and injection of drug. A tracheotomy is performed and respiration provided by a Harvard Model 681 respirator at a rate of approximately 55/min and a volume of 4 cc per cycle. The rat was then placed upon its right side and the heart was exposed by making an incision and separating the ribs. 4-0 Silk on taper RB-1 needle was passed under the left anterior descending coronary artery (LAD) at a location just under the tip of the left aterial appendage. The suture was left to be tied upon occlusion.

The rat was allowed to stabilize for 5 to 15 minutes before the administration of drug as a bolus via the cannulated jugular vein. The total drug dose volume is kept constant between 0.20–0.25 ml. Fifteen minutes after dosing, the LAD was occluded by tying the suture. This procedure provokes severe ventricular arrhythmias, terminating in ventricular fibrillation and death in at least about 65 percent of animals given vehicle only. The development and progression of ventricular arrhythmia is monitored for a period of 20 minutes.

Lead II ECG and cardiotachometer output were recorded on a Backman R612 recorder.

Mean arterial pressure (MAP) is monitored throughout the experiment, and the following values recorded: (1) MAP prior to drug, (2) maximal change in MAP following drug and before LAD occlusion, and (3) MAP just prior to LAD occlusion. Changes in cardiac electrical activity are determined from the Lead II electrocardiogram. The dysrhythmias are scored as follows: (1) normal sinus rhythm, (2) isolated premature ventricular complexes, (3) non-sustained ventricular tachycardia (repetitive beats of ventricular origin lasting $\leq 15$ sec.), (4) sustained ventricular tachycardia (repetitive ventricular activity lasting $\geq 15$ sec.), (5) self-terminating or reversible ventricular fibrillation (VFrev), and (6) irreversible VF (VF irrev. death). The incidence of death in the drug-treated group is then compared to that in the untreated control group (generally $\geq 65\%$). Five animals are included in each drug group.

Arrhythmias scores are calculated for each group of animals for purposes of obtaining more quantitative rankings for anti-arrhythmic efficacy. The equation, $$\sum_{o=1}^{i} A \times AS,$$

is used, where A=fraction of animals with a certain kind of arrhythmia (e.g., ventricular fibrillation, sustained ventricular tachycardia) and AS is the arbitrary score assigned to that arrhythmia:

|     | A                                      | AS  |
| --- | -------------------------------------- | --- |
| (a) | no arrhythmia                          | −5  |
| (b) | isolated premature beats (PVC's)       | +5  |
| (c) | non-sustained ventricular tachicardia  | +10 |
| (d) | sustained ventricular tachycardia      | +20 |
| (e) | reversible ventricular fibrillation    | +40 |
| (f) | death                                  | +50 |

Thus, for the purpose of these coronary ligation (C.L.) experiments, a score from −5 (no arrhythmia) to 50 (death) is assigned to the response of each rat in a test group, based upon the number, type and severity of each response. The sum of the percent of animals at each response level times the point score assigned that response level equals the score value of the compound being tested. The lower the score, the more active the compound in preventing ventricular dysrhythmia.

Some of the anti-arrthythmic agents of this invention present a pure electrophysiologic Class I profile of anti-arrhythmic activity in that they inhibit transport through cardiae sodium channels. The compound of Example 1, representative of the Class I anti-arrhythmie compounds of this invention, demonstrates a greater potency relative to standard anti-arrhythmic agents such as quinidine, while causing less depression of ventricular conduction at anti-arrhythmic doses.

Other compounds of this invention display a Class III anti-arrhythmic profile. Of these, the products of Examples 12 and 13 are representative. The Class III antiarrhythmic activity was established in accordance with the following standard test procedure:

Bundles of free-running Purkinje fibers with attached myocardium obtained from either ventricle of adult dog heart were pinned without stretching to the bottom of a 10 ml tissue chamber and continuously superfused with oxygenated Tyrode's solution at a flow rate of 10 ml/min. The composition of the Tyrode's solution was (mM): NaCl 150; KCl 4.0; CaCl$_2$ 2.7; MgCl$_2$ 0.5; HEPE buffer (7.4) 10; dextrose 5.5. The solution was acrated with 100% O$_2$. Bath temperature was maintained at 36°±0.5° C. by circulating the superfusate through a thermostatically controlled water bath immediately prior to entering the tissue chamber.

Preparations were stimulated through bipolar Teflon-coated platinum wires, bared at the tips, placed on the endocardial surface of the attached myocardium, using a W.P.I. digital stimulator set to deliver constant current pulses 1–2 msec in duration at cycle lengths (c.l.) of 330 or 1000 msec. Stimulus strength was set at approximately 2× diastolic threshold, and adjusted as required throughout the experiment. All preparations were allowed to equilibrate in the tissue chamber for at least 1 hour before measurements were begun. Subsequently, a minimum of 60 minutes was allowed for equilibration with each drug-containing superfusate before post-drug measurements were made. Impalements were made at 6–10 sites throughout the preparation before and after drug exposure. Offset potentials were re-checked at the conclusion of each experiment.

Glass microelectrodes filled with 3M KCl were coupled to high impedance negative capacitance electrometers (W.P. Instruments, New Haven, CT), and Ag-/AgCl half-cells used as reference electrodes. The first derivative of the action potential upstroke ($\dot{V}$max) was obtained using an analog differentiator circuit, coupled to a peakhold circuit that retained the recorded value of $\dot{V}$max for 30–70 msec. Action potential and Vmax tracings were displayed on a Tektronix storage oscilloscope, and photographed for later analysis. In addition, chart paper recordings of $\dot{V}$max were obtained using the peak-hold device output.

Fresh stock solutions of drug were prepared for each experiment. Compounds were dissolved in distilled water at total concentrations of 1–10 mg/ml, and subsequently diluted to a final concentration of 3 $\mu$M in appropriate volumes of normal Tyrode's solution for evaluation.

Action potential (AP) parameters measured included: diastolic take-off potential (or activation voltage, V$_{act}$); AP overshoot (V$_{os}$); AP duration measured as the time taken to repolarize to −20 mV (APD$_{20}$), −60 mV(APD$_{60}$), and −80 mV(APD$_{80}$); and maximal upstroke velocity ($\dot{V}$max). Data were compared using a two-sample t-test, with statistical significance taken as p<0.05. An increase in APD$_{60}$ that occurred without a significant change in $\dot{V}$max was taken, by definition, to indicate Class III anti-arrhythmic activity.

Based upon the activity profile elicited by the compounds of this invention in the above-described standard scientifically recognized test models, the compounds are established as anti-arrhythmic agents useful in the treatment of cardiac arrhythmias and conditions characterized by coronary arteries vasopasm. For that purpose, the compounds may be administered orally or parenterally in suitable dosage forms compatable with the route of administration, whether oral, intraperitoneal, intramuscular, intravenous, intrannsal, buccal, etc. The effective dose range determined in the animal test models has been established at from about 2 to about 20 milligrams per kilogram host body weight (preferably from 2 to 10 mg/kg) i.v., and from about 40 to about 100 mg/kg (preferably 40 to 50 mg/kg) p.o., to be administered in single or plural doses as needed to relieve the arrhythmatic dysfunction. The specific dosage regimen for a given patient will depend upon age, pathological state, serverity of dysfunction, size of the patient, etc. Oral administration is performed with either a liquid or solid dosage unit in any conventional form such as tables, capsules, solutions, etc., which coprise a unit dose (e.g. from about 2 milligrams to about 100 milligrams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the relative score for the compound produced, obtained in the coronary artery ligation experiments and the change in action potential duration and upstroke velocity, where tested, are provided.

EXAMPLE 1

4-Amino-N-(1-methylethyl)-N-[2[(1-methylethyl)amino)]ethyl]benzenesulfonamide p-Nitrobenzenesulfonyl chloride (22.1 g, 0.1 mole) in methylene chloride (150 ml) was added dropwise with stirring to N,N'-diisopropyl ethylene diamine (14.4 g, 0.1 mole) and triethylamine (10.1 g, 0.1 mole) in methylene chloride (400 ml). The reaction was stirred one hour at room temperature, washed with water and the solvent removed. The residue dissolved in diethyl ether precipitated the unwanted "bis"by-product which was filtered and discarded. Chromatography of the filtrate on Dry Column Silica Gel (500 g) with ethyl acetate provided pure product free base, N-(1-methylethyl)-N-[2-(1-methylethylamino)ethyl]-4-nitrobenzene sulfonamide, as a gum (14.31 g).

Analysis for: $C_{14}H_{24}N_3O_4SCl$: Calculated: C, 45.96; H,6.61; N, 11.48. Found: C, 46.53; H, 6.59; N, 11.39.

The compound made by the method of the preceding paragraph (19.09 g) in absolute ethanol (110 ml) containing platinum oxide (1.0 g) was shaken with hydrogen at three atmospheres for one and one half hours. The reaction was filtered and the solvent removed to provide a dark red gum. Trituration with diethyl ether produced the product as a crystalline solid (14.58 g) m.r. 90°–92° C.

Analysis for: $C_{14}H_{25}N_3O_2S$: Calculated: C, 56.16; H, 8.42; N, 14.03. Found: C, 55.90; H, 8.39; N, 13.82.

Score =8.

3 μM, 1000 msec c.l. %ΔAPD$_{60}$=−6.1; %ΔVmax=−8.7

EXAMPLE 2

4-Amino-N-(1-methylethyl)-N-[2-[(1-methylethyl)amino]ethyl]-benzenesulfonamide phosphate salt 4-Amino-N-(1-methylethyl)-N-[2-[(1-methylethyl)amino]ethyl]benzenesulfonamide (3.30 g, 0.011 mole) was dissolved in absolute acetone (20 ml) and $H_3PO_4$ (87%) (0.011 mole, 1.23 g) was added. Diethyl ether was added with stirring and scratching. Chilling and filtration produced the product (3.84 g) m.r. 215°–217° C.

Analysis for: $C_{14}H_{25}N_3O_2S \cdot H_3PO_4$; Calculated: C, 42.31; H, 7.10; N, 10.57. Found: C, 42.13; H, 7.09; N, 10.25.

Score =10.

EXAMPLE 3

N-[4-[[(1-Methylethyl)-[2-[(1-methylethyl)amino]ethyl]amino]sulfonyl]phenyl]acetamide 4-Acetaminobenzene sulfonyl chloride (23.3 g, 0.1 mole) as a slurry in 400 ml methylene chloride was added to N,N'-diisopropyl ethylene diamine (14.46 g, 0.1 mole) and triethylamine (10.1 g, 0.1 mole) in methylene chloride (600 ml). The reaction was stirred overnight at room temperature. The reaction was washed with water, insoluble by-product filtered off, and the filtrate stripped to a brown gum. After filtration through silica gel in 20% MeOH/EtOAc the crude crystalline product was recrystallized from isopropanol to provide the title product as the hydrochloride salt (3.00 g, m.r. 176°–178° C.).

Analysis for: $C_{16}H_{27}N_3O_3S \cdot HCl$ Calculated: C, 50.85; H, 7.46; N, 11.12. Found: C, 51.05; H, 7.44; N, 10.95.

Score=22.

EXAMPLE 4

3-Amino-N-(1-methylethyl)-N-[2-[(1-methylethyl)amino]ethyl]benzenesulfonamide Following the procedure of Example 1, m-nitrobenzenesulfonyl chloride was reacted with N,N'-diisopropyl ethylene diamine to give N-(1-methylethyl)-N-[2-[(1-methylethyl)amino]ethyl]-3-nitrobenzene sulfonamide.

Analysis for: $C_{14}H_{24}ClO_4N_3S$; Calculated: C, 45.96; H, 6.61; N, 11.48. Found: C, 45.86; H, 6.65; N, 11.30.

The product of the preceding paragraph (21.75 g) in absolute ethanol (180 ml) and $PtO_2$ (1.0 g) was shaken with hydrogen for 2.5 hours. Workup gave a crude gum which was dissolved in diethyl ether, filtered and the solvent removed to provide the product (20.0 g). Solution in ether and standing overnight provided the free base as a crystalline solid (11.45 g) m.r. 105°–108° C. (d). A portion of this material dissolved in isopropanol was treated with maleic acid to provide the di-maleate salt of the title compound, m.r. 140°–142° C.

Analysis for: $C_{14}H_{25}N_3O_2S \cdot 2C_4H_4O_4$. Calculated: C, 49.71; H, 6.26; N, 7.90. Found: C, 49.83; H, 6.32; N, 8.12. Score=22.

EXAMPLE 5

4-Amino-N-(1-methylethyl)-N-[3-[(1-methylethyl)amino]propyl]benzenesulfonamide, maleate To N,N'diisopropyl propane-1,3-diamine (23.43 g) in methylene chloride was added p-nitrobenzenesulfonyl chloride (11.08 g, 0.5 mole) dropwise and the reaction stirred 2 hours. The reaction was filtered, stripped, the residue dissolved in diethyl ether, refiltered after washing with water and the contents of the filtrate chromatographed on dry column silica gel with ethyl acetate to provide 9.75 g of clear product as the free base, N-(1-methylethyl)-N-[3-(1-methylethylamino)propyl]-4-nitrobenzene sulfonamide, characterized as the hydrochloride, m.r. 183°–185° C.

Analysis for: $C_{15}H_{26}ClO_4N_3S$. Calculated: C, 47.42; H, 6.90; N, 11.06. Found: C, 47.77; H, 6.82; N, 10.97.

Hydrogenation of the product of the preceding paragraph using $PtO_2/H_2$/MeOH followed by purification and conversion to the maleate salt gave a white solid, m.r. 140°–142° C.

Analysis for: $C_{19}H_{31}N_3O_6S$. Calculated: C, 53.13; H, 7.28; N, 9.78. Found: C, 52.75; 11, 6.94; N, 9.53.

EXAMPLE 6

4-Amino-N-[(1,1-dimethyl-2-[(1-methylethyl)amino]ethyl]benzenesulfonamide

Following the procedure of Example 1, p-nitrobenzenesulfonyl chloride was reacted with N'-isopropyl 2-methyl-1,2-propane diamine to obtain 4-nitro-N-[1,1-dimethyl-2-[(1-methylethyl)amino]ethyl]benzenesulfonamide. The product was hydrogenated to afford the title compound, m.r. 138°–140° C.

Analysis for: $C_{13}H_{23}N_3O_2S$. Calculated: C, 54.71; H, 8.12; N, 14.72. Found: C, 54.17; H, 8.04; N, 14.22.

EXAMPLE 7

4-Amino-N-[2-(diethylamino)ethyl]-N(1-methylethyl)-benzenesulfornamide p-Nitrobenzene sulfonyl chloride (22.1 g, 0.1 mode) in methylenechloride (200 ml) was added dropwise to N,N-diethylethylene diamine (11.6 g, 0.1 mole) and triethylamine (10.1 g, 0.1 mole) in methylene chloride. The reaction was stirred two days, washed with water, then brime and the solvent removed. The solid residue was dissolved in diethyl ether, filtered through Supercel®, hexane added and N-[2-(diethylamino)ethly]-N-(1-methylethyl)-4-nitrobenzene sulfonamide obtained by stirring and chilling (18.54 g) m.r. 56°–57° C.

Analysis for: $C_{15}H_{25}N_3O_4S$. Calculated: C, 52.46; H, 7.34; N, 12.23. Found: C, 52.24; H, 7.21; N, 11.89.

The product of the preceding paragraph (8.46 g) in ethanol (80 ml) and $PtO_2$ (0.35 g) was shaken under hydrogen for 2.5 hours. Workup and recrystallization from diethyl ether/hexane provided the product as a white solid (7.00 g) m.r. 94°–95° C.

Analysis for: $C_{15}H_{27}N_3O_2S$. Calculated: C, 57.48; H, 8.68; N, 13.40. Found: C, 57.67; H, 8.64; N, 13.40 Score=20.

EXAMPLE 8

4-Amino-N-[2-[(1-methylethyl)amino]ethyl]benzenesulfonamide p-Nitrobenzenesulfonyl chloride was reacted with n-isopropyl ethylene diamine to provide the crystalline free base, N-[2-[(1-methylethyl)amino]ethyl]-4-nitrobenzene sulfonamide, m.r. 143°–145° C.; characterized as the hydrochloride salt, m.r. 203°–205° C.

Analysis for: $C_{11}H_{18}N_3O_4SCl$: Calculated: C, 40.80; H, 5.60; N, 12.98. Found: C, 40.91; H, 5.67; N, 12.80.

The free base was hydrogenated and the title compound was isolated as a crystalline solid, m.r. 72°–74° C., and converted to the maleate in isopropanol, m.r. 162°–164° C.

Analysis for: $C_{11}H_{19}N_3O_2S.C_4H_4O_4$: Calculated: C, 48.25; H, 6.21; N, 11.25. Found: C, 48.66; H, 5.94; N, 10.89.

EXAMPLE 9

4-(Methylamino)-N-(1-methylethyl)-N-[2-[(1-methylethyl)-amino]ethyl]benzenesulfonamide 4-(Dimethylamino)benzenesulfonic acid, sodium slat (37.1 gm, 0.195 mol) was treated with thionyl chloride (100 gm) containing dimethylformamide (1.0 gm) and the emerald green solution heated for four hours. Benzene (300 ml) was added and the mixture rotated to dryness. Successive rotations with benzene and toluene removed the thionyl chloride. There remained a greenish solid (49.66 gm) this was treated with N,N'-diisopropyl diamine (36.34 gm) and triethylamine (19.7 gm) in methylene chloride (500 ml). After stirring overnight the solution was washed with aqueous sodium hydroxide and then brine. Removal of solvent, dissolution in diethyl ether, filtration and removal of solvent provided a mixed product gum (46.10 gm). Isolated from this mixture was the title compound as flakes (0.81 gm), m.r. 126°–128° C. from diethyl ether/$CH_2Cl_2$.

Analysis for: $C_{15}H_{27}N_3O_2S$: Calculated: C, 57.48; H, 8.68; N, 13.40. Found: C, 57.44; H, 8.72; N, 12.93.

EXAMPLE 10

4-Amino-N-[2-[bis(1-methylethyl)amino]ethyl]-N-(1-methylethyl)benzenesulfonamide p-Nitrobenzenesulfonyl chloride was reacted with N,N',N'-triisopropyl ethylene diamine to obtain the free base of N-[2-[bis(1-methylethyl)amino]ethyl]-N-(1-methylethyl)-4-nitrobenzene sulfonamide as a yellow solid, m.r. 98°–100° C.

Analysis for: $C_{17}H_{29}N_3O_4S$: Calculated: C, 54.96; H, 7.87; N, 11.31. Found: C, 54.43; H, 7.67; N, 11.66.

The product of the preceding paragraph was reduced catalytically in the system Pt/$H_2$/tetrahydrofuran. Isolated from the product mixture was the title compound which was crystallized from isopropanol, m.r. 100°–102° C.

Analysis for: $C_{17}H_{31}N_3O_2S$: Calculated: C, 59.79; H, 9.15; N, 12.30. Found: C, 59.54; H, 9.16; N, 12.22.

EXAMPLE 11

4-Amino-N-[2-[bis(1-methylethyl)amino]ethyl]benzenesulfonamide p-Nitrobenzenesulfonyl chloride was reacted with N,N-diisopropyl ethylene diamine to give N-[2-[bis(1-methylethyl)amino]ethyl]-4-nitrobenzene sulfonamide as the free base, m.r. 86°–88° C.

Analysis for: $C_{14}H_{23}N_3O_4S$: Calculated: C, 51.05; H, 7.04; N, 12.76. Found: C, 51.34; H, 7.15; N, 12.66.

The product of the preceding paragraph was catalytically reduced in methanol/$PtO_2$ to provide the title compound, m.r. 115°–117° C.

Analysis for: $C_{14}H_{25}N_3O_2S$: Calculated: C, 56.16; H, 8.42; N, 14.03. Found: C, 56.23; H, 8.46; N, 14.10.

EXAMPLE 12

4-Acetamino-N-[2-[bis(1-methylethyl)amino]ethyl]N-(1-methylethyl)benzenesulfonamide The title compound was prepared by the procedure of Example 3, starting with p-acetaminobenzene sulfonyl chloride and the Appropriate amine to give the solid free base, m.r. 150°–151° C.

Analysis for: $C_{19}H_{33}N_3O_3S$: Calculated: C, 59.50; H, 8.67; N, 10.96. Found: C, 59.92; H, 8.73; N, 10.98.

Hydrochloride salt, m.r. 196°–198° C.

Analysis for: $C_{19}H_{33}N_3O_3S.HCl$: Calculated: C, 54.33; H, 8.16; N, 10.00. Found: C, 53.99; H, 8.05; N, 9.68.

3 $\mu M$, 1000 msec c.l.: %$\Delta APD_{60}$ =5.2; %$\Delta \dot{V}max$=7.8.

EXAMPLE 13

4-Acetamino-N-[2-[bis(1-methylethyl)amino]ethyl]benzenesulfonamide

Following the procedure of Example 12, 4-acetaminobenzene sulfonyl chloride was reacted with N,N-diisopropylethylene diamine. The free base was isolated, m.r. 112°–115° C. and converted to the hydrochloride salt, m.r. 203°–205° C.

Analysis for: $C_{16}H_{28}N_3O_3SCl$: Calculated: C, 50.85; H, 7.47; N, 11.12. Found: C, 50.77; H, 7.71; N, 10.90.

3 µM, 1000 msec c.l.: %ΔAPD$_{60}$ =9.2; %ΔVmax=7.1.

What is claimed is:

1. A compound of the formula

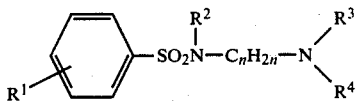

in which
- $R^1$ is —NH$_2$ or alkylamino of 1 to 3 carbon atoms, in 3- or 4-position of the benzene ring;
- $R^2$ is branched chain alkyl of 3 or 4 carbon atoms;
- $R^3$ is hydrogen or straight or branched chain alkyl of 1 to 4 carbon atoms;
- $R^4$ is straight or branched chain alkyl of 1 to 4 carbon atoms; and
- n is one of the integers 2, 3 or 4;

or a pharmaceutically acceptable salt thereof.

2. A compound of the formula

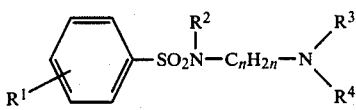

in which
- $R^1$ is alkanoylamino of 2 to 4 carbon atoms, in 3- or 4-position of the benzene ring;
- $R^2$ is hydrogen or branched chain alkyl of 3 or 4 carbon atoms;
- $R^3$ is hydrogen or straight or branched chain alkyl of 1 to 4 carbon atoms;
- $R^4$ is straight or branched chain alkyl of 1 to 4 carbon atoms; with the proviso that $R^3$ and $R^4$ are branched chain alkyl when $R^2$ is hydrogen; and
- n is one of the integers 2, 3 or 4;

or a pharmaceutically acceptable salt thereof.

3. A compound of claim 1 which is 4-amino-N-(1-methylethyl)-N-[2-[(1-methylethyl)amino]ethyl]benzenesulfonamide or a pharmaceutically acceptable salt thereof.

4. A compound of claim 2 which is N-[4-[[(1-methylethyl)-[2-[(1-methylethyl)-amino]ethyl]amino]sulfonyl]phenyl]acetamide or a pharmaceutically acceptable salt thereof.

5. A compound of claim 1 which is 3-amino-N-(1-methylethyl)-N-[2-[(1-methylethyl)amino]ethyl]benzenesulfonamide or a pharmaceutically acceptable salt thereof.

6. A compound of claim 1 which is 4-amino-N-(1-methylethyl)-N-[3-[(1-methylethyl)amino]propyl]benzenesulfonamide or a pharmaceutically acceptable salt thereof.

7. A compound of claim 1 which is 4-amino-N-[2-(diethylamino)ethyl]-N-(1-methylethyl)benzene or a pharmaceutically acceptable salt thereof.

8. A compound of claim 1 which is 4-(methylamino)-N-(1-methylethyl)-N-[2-[(1-methylethyl)amino]ethyl]benzenesulfonamide or a pharmaceutically acceptable salt thereof.

9. A compound of claim 1 which is 4-amino-N-[2-[bis(1-methylethyl)amino]ethyl]N-(1-methylethyl)benzenesulfonamide or a pharmaceutically acceptable salt thereof.

10. A compound of claim 2 which is 4-acetamino-N-[2[bis(1-methylethyl)amino]ethyl]N-(1-methylethyl)-benzenesulfonamide or a pharmaceutically acceptable salt thereof.

11. A compound of claim 2 which is 4-acetamino-N-[2-[bis(1-methylethyl)amino]ethyl]benzenesulfonamide or a pharmaceutically acceptable salt thereof.

12. A compound of claim 1 of the formula

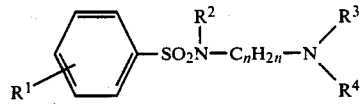

in which
- $R^1$ is —NH$_2$ or alkylamino of 1 to 3 carbon atoms, in 3- or 4-position of the benzene ring;
- $R^2$ and $R^4$ are, independently, branched chain alkyl of 3 or 4 carbon atoms;
- $R^3$ is hydrogen or branched chain alkyl of 3 or 4 carbon atoms; and
- n is one of the integers 2, 3 or 4;

or a pharmaceutically acceptable salt thereof.

* * * * *